US011058892B2

(12) United States Patent
Wilbur et al.

(10) Patent No.: US 11,058,892 B2
(45) Date of Patent: Jul. 13, 2021

(54) REVOLVING RADIATION COLLIMATOR (71) Applicant: Zap Surgical Systems, Inc., San Carlos, CA (US)

(72) Inventors: Raymond Wilbur, San Jose, CA (US); Younes Achkire, San Francisco, CA (US); Manoocher Birang, San Carlos, CA (US)

(73) Assignee: Zap Surgical Systems, Inc., San Carlos, CA (US)

( * ) Notice: Subject to any disclaimer, the term of this patent is extended or adjusted under 35 U.S.C. 154(b) by 381 days.

(21) Appl. No.: 15/971,861

(22) Filed: May 4, 2018

(65) Prior Publication Data

US 2018/0318607 A1 Nov. 8, 2018

Related U.S. Application Data (60) Provisional application No. 62/502,472, filed on May 5, 2017.

(30) Foreign Application Priority Data

Jun. 20, 2017 (WO) ................ PCT/US2017/038256

(51) Int. Cl.
*A61N 5/10* (2006.01)
*G21K 1/02* (2006.01)
(Continued)

(52) U.S. Cl.
CPC ......... *A61N 5/1042* (2013.01); *A61N 5/1081* (2013.01); *G01B 11/27* (2013.01);
(Continued)

(58) Field of Classification Search
CPC .......... A61N 5/1042–1047; A61N 2005/1092–1096; G21K 1/02–046
See application file for complete search history.

(56) References Cited

U.S. PATENT DOCUMENTS

| 3,852,598 A | 12/1974 | Larsson |
| 4,266,135 A | 5/1981 | Kuwik et al. |
(Continued)

FOREIGN PATENT DOCUMENTS

| CN | 1481756 | 3/2004 |
| CN | 1666301 | 9/2005 |
(Continued)

OTHER PUBLICATIONS

Weidlich et al., "Characterization of a Novel Revolving Radiation Collimator", Cureus, vol. 10, No. 2, Feb. 2, 2018, pp. 1-9.

*Primary Examiner* — Thaddeus B Cox
(74) *Attorney, Agent, or Firm* — Kilpatrick Townsend & Stockton LLP (57) ABSTRACT

Devices, systems and method that allow for delivery of therapeutic radiation beams of differing sizes or shapes during a radiation treatment are provided herein. Such devices can include a rotatable collimator body having multiple collimator channels of differing size or shape defined therein, the channels extending through the collimator body substantially perpendicular to the axis of rotation. The collimator body can include markers thereon to facilitate detection of an alignment position by a sensor of a control system to allow the collimator body to be rapidly and accurately moved between alignment positions to facilitate delivery of differing therapy beams during a treatment.

20 Claims, 5 Drawing Sheets (51) Int. Cl.
*G21K 1/04* (2006.01)
*G01B 11/27* (2006.01)
(52) U.S. Cl.
CPC .............. *G21K 1/025* (2013.01); *G21K 1/046* (2013.01); *A61N 2005/1095* (2013.01)

(56) References Cited

U.S. PATENT DOCUMENTS

| | | | |
|---|---|---|---|
| 5,054,041 A | 10/1991 | Hampel | |
| 5,945,684 A | 8/1999 | Lam et al. | |
| 8,139,714 B1 | 3/2012 | Sahadevan | |
| 9,014,341 B2 | 4/2015 | Zhang et al. | |
| 9,208,918 B2 | 12/2015 | Tybinkowski et al. | |
| 9,308,395 B2 | 4/2016 | Adler, Jr. et al. | |
| 9,314,160 B2 | 4/2016 | Adler, Jr. et al. | |
| 9,604,077 B2 | 3/2017 | Xing et al. | |
| 2004/0066889 A1* | 4/2004 | Swift | G21K 1/04 378/57 |
| 2004/0251419 A1 | 12/2004 | Nelson et al. | |
| 2005/0236588 A1 | 10/2005 | Ein-gal | |
| 2006/0245548 A1* | 11/2006 | Callerame | G01N 23/203 378/160 |
| 2008/0212738 A1* | 9/2008 | Gertner | A61N 5/1077 378/65 |
| 2009/0086909 A1 | 4/2009 | Hui et al. | |
| 2009/0103686 A1* | 4/2009 | Rothschild | G21K 1/043 378/160 |
| 2009/0110146 A1 | 4/2009 | Sliski et al. | |
| 2010/0094119 A1* | 4/2010 | Yu | G01R 33/4808 600/411 |
| 2010/0237259 A1 | 9/2010 | Wang | |
| 2013/0136239 A1 | 5/2013 | Laws et al. | |
| 2013/0188856 A1 | 7/2013 | Adler, Jr. et al. | |
| 2013/0261430 A1 | 10/2013 | Uhlemann | |
| 2014/0140471 A1 | 5/2014 | Tybinkowski et al. | |
| 2016/0095558 A1 | 4/2016 | Choy et al. | |
| 2016/0220848 A1 | 8/2016 | Adler, Jr. et al. | |
| 2016/0317839 A1 | 11/2016 | Prionas et al. | |
| 2017/0281972 A1* | 10/2017 | Zhang | A61B 6/06 |
| 2018/0318607 A1 | 11/2018 | Wilbur et al. | |
| 2019/0001146 A1* | 1/2019 | Liu | A61N 5/1081 |
| 2020/0038685 A1* | 2/2020 | Kundapur | A61N 5/1045 |

FOREIGN PATENT DOCUMENTS

| | | | |
|---|---|---|---|
| CN | 106512221 | 3/2017 | |
| DE | 19728788 A1 | 1/1999 | |
| JP | 6082300 U | 6/1985 | |
| JP | 0767975 | 3/1995 | |
| NL | 7215879 | 5/1973 | |
| WO | 2012040964 | 4/2012 | |
| WO | 2013180883 | 12/2013 | |
| WO | WO-2015096572 A1 * | 7/2015 | ........... A61N 5/1077 |
| WO | 2017020244 | 2/2017 | |
| WO | 2017041750 | 3/2017 | |
| WO | 2017100611 A1 | 6/2017 | |
| WO | 2018/203918 A1 | 11/2018 | |

\* cited by examiner

REVOLVING RADIATION COLLIMATOR

CROSS-REFERENCES TO RELATED APPLICATIONS

The present application claims the benefit of priority of U.S. Provisional Application No. 62/502,472 filed May 5, 2017 and PCT Application Serial No. PCT/US2017/038256 filed Jun. 20, 2017, the entire contents of which are incorporated herein by reference.

The present application is related to PCT Application Serial No. PCT/US/2017/054880 filed Oct. 3, 2017, which is assigned to the same assignee as the present application and incorporated by reference herein in its entirety for all purposes.

BACKGROUND

The overarching goal of the collimator system is to deliver a beam of radiation produced by a source (for example a LINAC) to a target (for example a tumor in a patient's brain). Because it is desirable to irradiate a tumor, but generally not desirable to irradiate surrounding healthy tissue, the size and the shape of each beam is of critical importance. In order to control the shape (for example diameter or 2D cross sectional area) of a beam of radiation, a collimator is used. A collimator is generally a piece of dense radiopaque metal that substantially blocks a beam of radiation except where a formed or machined hole allows the radiation to be transmitted through. A larger radiation footprint may be produced by the radiation source (for example a LINAC or cobalt), but only those particles aligned to pass through the collimator will be permitted through to reach the target, the excess being absorbed or scattered internally. In addition to the tubular channels of machined or formed collimators, another pre-existing type is a "multi leaf collimator" using multiple thin tungsten plates moving in and out of the beam path to generate the desired beam exposure shape during treatment. This complex mechanism is complex, bulky, expensive, and prone to mechanical failure.

Different size and shape radiation treatment targets require different size and shape beams of radiation. There exists a need for systems and methods that allow for radiation beams to be changed in a rapid and predictable manner. There is a need for collimating radiation beams without excess leakage of radiation around the collimator. There is further a need for such systems to remain small, reliable and low cost.

BRIEF SUMMARY

The invention relates to the field of radiation therapy, and in particular, to collimator systems and associated methods of controlling the size and shape of radiation treatment beams during radiation therapy.

In a first aspect, the invention pertains to a radiation collimator assembly that includes a rotatable collimator body or collimator wheel having multiple collimator channels defined therein. In some embodiments, the collimator channels extend longitudinally perpendicular to the rotational axis of the collimator wheel, extending from the perimeter of the wheel, passing through the center and out to the opposite perimeter of the wheel. The collimator wheel is at least partly surrounded by a collimator shield, excepting at least the portion having the selected collimator channel that is aligned with the radiation source and the patient target to allow passage of the radiation beam therethrough. In some embodiments, the posterior, LINAC-facing portion of the collimator wheel is ensheathed in shielding to prevent stray radiation from passing through non-selected collimator channels. The collimator shield is fabricated from a suitable radiation absorptive material, typically tungsten or tungsten alloy, so as to block and absorb any scattered radiation emitted from orifices of non-aligned channels.

In another aspect, the collimator body is motorized and precisely indexed for rapid and exacting computer-controlled positioning of the selected collimator channel geometry with the radiation source, thereby delivering a desired beam shape to the precise dimensions required at the target. By using a revolving collimator wheel, multiple sizes of the beam may be utilized during one treatment, quickly and automatically switching between two or more selected collimators.

These collimation assemblies have the advantage of being rapidly changeable by computer control, while remaining small, reliable in their simplicity and low in cost. Moreover, such assemblies can utilize a single motor to switch between select one or more collimator channels. The aspects of the invention described herein allow for a more reliable radiation collimator that can quickly and precisely change X-ray exposure from 1 mm to 30 mm diameter at isocenter, and can function more reliably than many prior art collimators. Such collimator assemblies enable rapid, automated (motorized and computer controlled) changing of beam aperture in the service of therapeutic radiation delivery, for example to treat brain tumors.

The collimator systems described herein allow for beam collimation without requiring use of a conventional block collimator and/or multi-leaf collimator system, such as those commonly used in conventional radiation treatment systems, which are bulky and prone to mechanical malfunction over time.

In one aspect, an exemplary radiation collimator assembly includes a radiation source and a collimator wheel rotatable about a rotational axis thereof. The collimator wheel has multiple collimator channels that include a first and second collimator channel defined within the collimator wheel that are arranged substantially perpendicular to the rotational axis of the collimator wheel. The collimator can include additional channels, for example three or more channels. The collimator can include any number of channels desired (e.g. 2, 3, 4, 5, 6, 7, 8, 9, 10 channels or more). In some embodiments, each of the first and second collimator channels pass through a center of the collimator wheel through which the rotational axis extends. Preferably, at least some of the collimator channels are of differing sizes and/or shapes. In some embodiments, the multiple collimator channels are distributed at regular intervals along the collimator wheel.

In another aspect, the first and second collimator channels are selectable by rotationally moving the collimator wheel to align one of the first and second collimator channels with the radiation source. Selective rotation of the collimator wheel can be facilitated by a motor and control unit operably coupled to the wheel. In some embodiments, the collimator assembly includes a motor operably coupled with the collimator wheel so as to rotate the collimator wheel about the rotational axis; and a control unit operably coupled with the motor to control rotation of the collimator wheel to a collimator position corresponding to alignment of a selected collimator channel with the radiation source. In some embodiments, the control unit is communicatively coupled with one or more sensors configured to detect the collimator position. The one or more sensors can include one or more encoder readers and the collimator wheel includes multiple markers positioned thereon so that detection of a marker corresponds to alignment of a corresponding collimator channel.

In another aspect, radiation treatment systems utilizing such collimator assemblies are provided herein. An exemplary treatment system can include a radiation collimator assembly, such as described above, that is configured to deliver a radiation beam from a radiation source through one or more selected collimator channels of the collimator wheel to a target within a patient. Such a system can include a motor operably coupled with the collimator wheel so as to rotate the collimator wheel about the rotational axis and a control unit operably coupled with the motor to control rotation of the collimator wheel to positions corresponding to alignment of one or more selected collimator channel with the radiation source. The control unit is configured rotate the collimator wheel to align one or more selected collimator channels with the radiation source, the one or more selected collimator channels corresponding to one or more desired therapy beams.

In another aspect, the treatment system includes a collimator shield. The collimator shield can be configured to surround at least a portion of the collimator body during delivery of therapy so as to block radiation from non-aligned collimator channels while allowing passage of a therapy beam from the selected, aligned collimator channel. In some embodiments, the collimator shield substantially surrounds a portion of the collimator wheel facing the radiation source except for the entry orifice of the selected, aligned collimator channel. In some embodiments, the collimator shield substantially surrounds the collimator body except for an aperture at an apex of the shield through which includes the exit orifice of the selected aligned collimator channel is exposed as well as a passage at the inlet orifice of the aligned channel to allow entry of the radiation beam through the selected channel. While a conically shaped shield is depicted in the embodiments presented herein, it is appreciated that the collimator shield could be formed in various different shapes so long as the shield allows radiation to pass through the selected, aligned channel while blocking radiation emitted from non-selected channels and from around the shield itself, resulting in minimal radiation leakage around the intended beam.

In yet another aspect, the treatment system can include an alignment verification mechanism. Such a verification feature can include an optical alignment feature, such as an optical laser light mechanism that directs a laser light beam through the selected collimator channel and detects the laser light beam emanating from an exit orifice. In some embodiments, the treatment system further includes one or more imaging devices for monitoring a patient during treatment.

In some embodiments, the collimator includes a collimator body having a pivot feature about which the collimator body is rotatable about a pivotal axis and multiple collimator channels extending through the collimator body, each being substantially perpendicular to the pivotal axis about which the collimator body is revolved. In some embodiments, each of the multiple collimator channels intersects the pivotal axis.

In another aspect, methods of delivering therapy beams of differing size and/or shape to a target in a patient during therapy are provided herein. An exemplary method includes selecting a first collimator channel from multiple collimator channels in a collimator body, the selected first collimator channel corresponding to a desired first therapy beam. The collimator body is rotatable within the treatment system along a rotational axis of the collimator body and the multiple collimator channels differ in size and/or shape and extend substantially perpendicular to the rotational axis. Next, the collimator body is rotated along the rotational axis until the selected first collimator channel is aligned with the radiation source, then a first particle beam is transmitted from a radiation source through the selected first collimator channel so as to direct the desired first therapy beam to the target within the patient. Such methods can further include selecting a second collimator channel in the collimator body, the selected second collimator channel corresponding to a desired second therapy beam differing from the first therapy beam in size and/or shape. The collimator body is then rotated along the rotational axis until the selected second collimator channel is aligned with the radiation source and then a second particle beam is transmitted from the radiation source through the selected second collimator channel so as to direct the desired second therapy beam to the target within the patient. In some embodiments, rotating the collimator body until the selected first collimator channel is aligned comprises rotating the collimator body until a sensor of a control unit of the system detects a marker disposed on the collimator body indicating a collimator position that corresponds to alignment of the first collimator channel. Such methods can further include validating alignment of the first collimator channel with the radiation source by transmitting a laser light beam through the collimator channel and detecting the laser light beam emitted from an exit aperture of the first collimator channel.

Various aspects and details of the invention can be further understood by referring to the exemplary embodiments depicted in the figures and the description provided below.

DETAILED DESCRIPTION

The invention relates generally to radiation treatment systems and methods of use, in particular collimator systems provide selective control and delivery of collimated beams of radiation.

Figure 1:
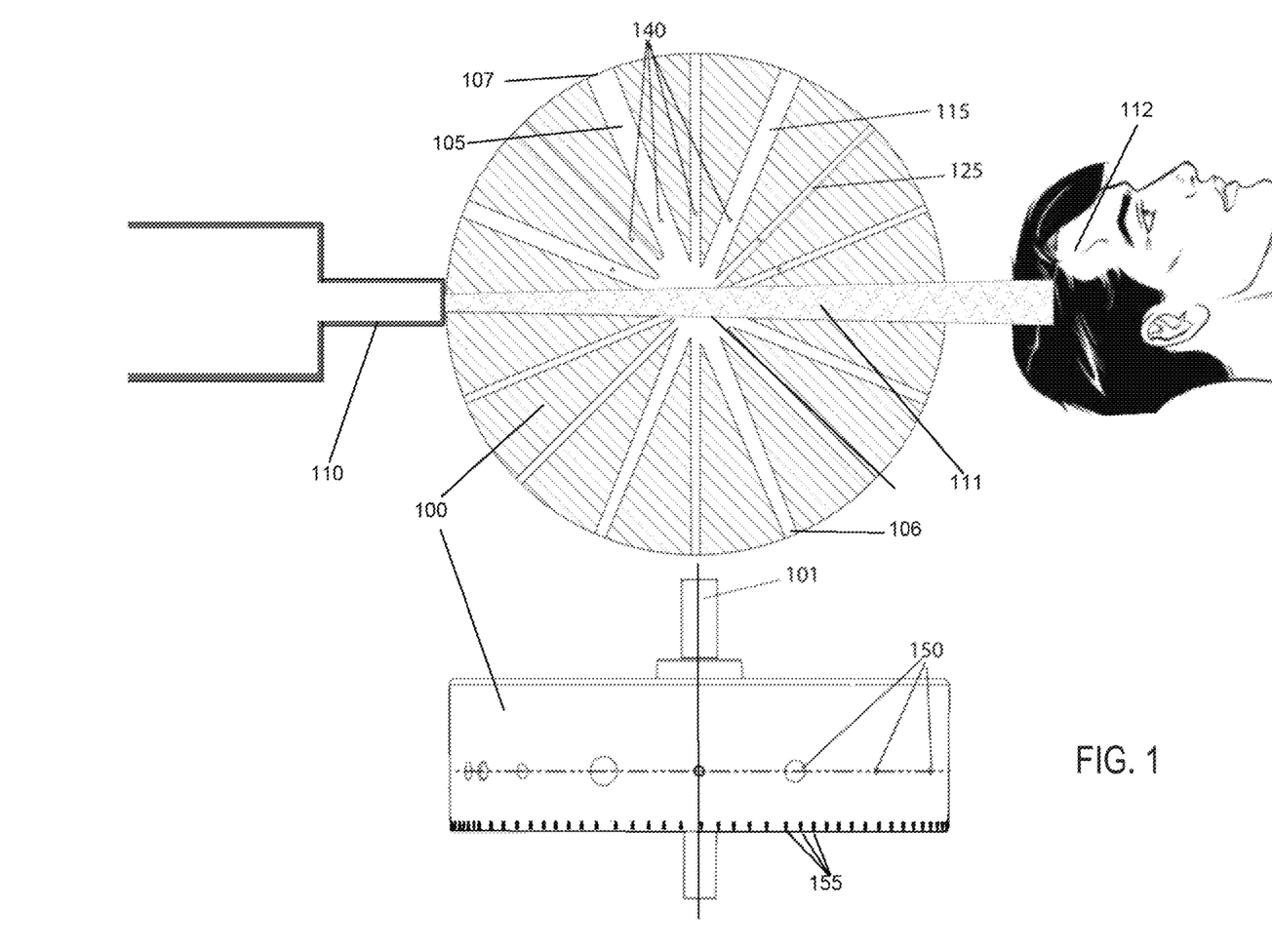
FIG. 1 shows a cross section of an example revolving collimator wheel having collimator channels passing therethrough.

FIG. 1 shows a cross sectional view of a revolving collimator wheel 100 having collimator channels 140 passing therethrough. Collimator wheel 100 has longitudinally extending channels or collimator channels 105, 115 and 125 defined therein, for example machined through the body of collimator wheel 100. The figure shows multiple other channels that are not labeled for the sake of clarity of the drawing. The collimator channels may be of various sizes, diameters or shapes. In some embodiments, each collimator channel is of a different diameter. For example, as shown in FIG. 1, collimator channel 105 is of larger bore than collimator channel 115, which is of larger bore than collimator channel 125. Each collimator channel extends from a radiation entrance aperture 106 to an exit aperture 107. In some embodiments, the size of the entrance aperture 106 is smaller than that of the exit aperture 107 to facilitate a sharp falloff of radiation dose at the margins of the irradiated area. The collimator wheel 100 is rotated so that a selected collimator channel is aligned with a radiation source 110 to allow passage of a particle radiation beam 111 through the selected channel, thereby providing a desired therapy beam to a target 112 in the patient. In a side profile of collimator wheel 100 shown at the bottom of FIG. 1, the entrance and exit apertures 150 are visible about the circumference collimator wheel 100 turns on axis 101. In this example, collimator wheel 100, couples with a 50:1 reduction gearbox and electric motor. In some embodiments, channel 105 and exit aperture 107 are round. It is appreciated that in alternative embodiments, the channels may be of any size or shape, for example square. Collimator wheel 100 can be formed of any suitable material, for example machined from a titanium alloy. While collimator wheel 100 is shown as being oriented vertically relative to the surface on which the patient rests, it is appreciated that the collimator wheel 100 could be configured in any orientation so long as the treatment beams passing through the collimator channels are directed to the target. Further, while the collimator wheel is shown as having eight collimator channels it is appreciated that such collimator wheels could include more or fewer collimator channels.

Figure 2:
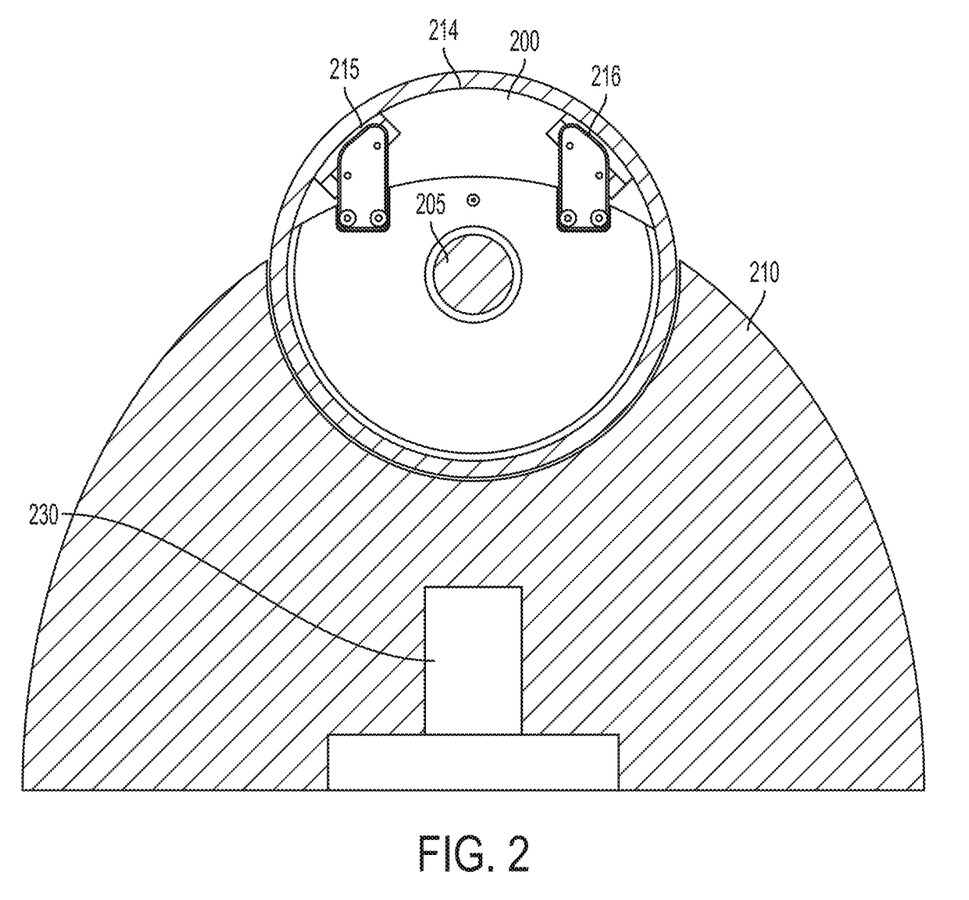
FIG. 2 shows an example revolving collimator wheel mounted upon a conical shield, the collimator wheel having magnetic encoder trackers that sense when the wheel has been brought into a desired collimator position.

FIG. 2 shows a cross section of a revolving collimator wheel 200 mounted upon a collimator shield 210, and rotating between collimator positions on axis 205. In this embodiment, the collimator shield 210 substantially ensheaths the portion of the collimator wheel facing the radiation source so as to prevent radiation from entering non-aligned collimator channels, and of a thickness designed to otherwise provide shielding against leakage for the radiation source. The rotational position of the collimator wheel can be precisely controlled by a control system by use of one or more sensors or encoders that monitor the position of the collimator wheel 200, for example by detecting markers disposed on the periphery of the collimator wheel. In this embodiment, the position of the collimator wheel is precisely monitored by encoder reader heads 215 and 216, which track a thin tape-like encoder strip affixed to the inner rim 214 of collimator wheel 100, adjacent to the path of reader heads 215 and 216. The control system detects signals produced by precisely placed changes in the electromagnetic interaction between the encoders and the encoder strip. Using this combination of encoder strip affixed to internal rim 214 and encoder reader heads, the control system senses when the wheel has been brought into the desired collimator position. Also shown in the cross section of collimator shield 210 is a LINAC head 230, which is the source of the radiation delivered to the entrance aperture of a selected collimator. In some embodiments, an ion chamber for measuring radiation intensity is included in the collimator shield between the LINAC head 230 and collimator wheel 200. Alternative positional encoder schemes could include mechanical stops such as gear teeth and divots, and/or optically sensed position markers.

In one aspect, the collimator assembly and control system described above are incorporated into a treatment system. The control system includes a processor configured to faciliate controlled rotation of the collimator wheel to select positions corresponding to alignment of a selected collimator channel with the radiation source, the selected collimator channel corresponding to a desired treatment beam. In some embodiments, the treatment system includes a user interface that allows a treating physician to select one or more treatment beams associated with one or more collimator channels. In other embodiments, the control system automatically determine one or more collimator channels corresponding to a selected course of treatment.

Figure 3:
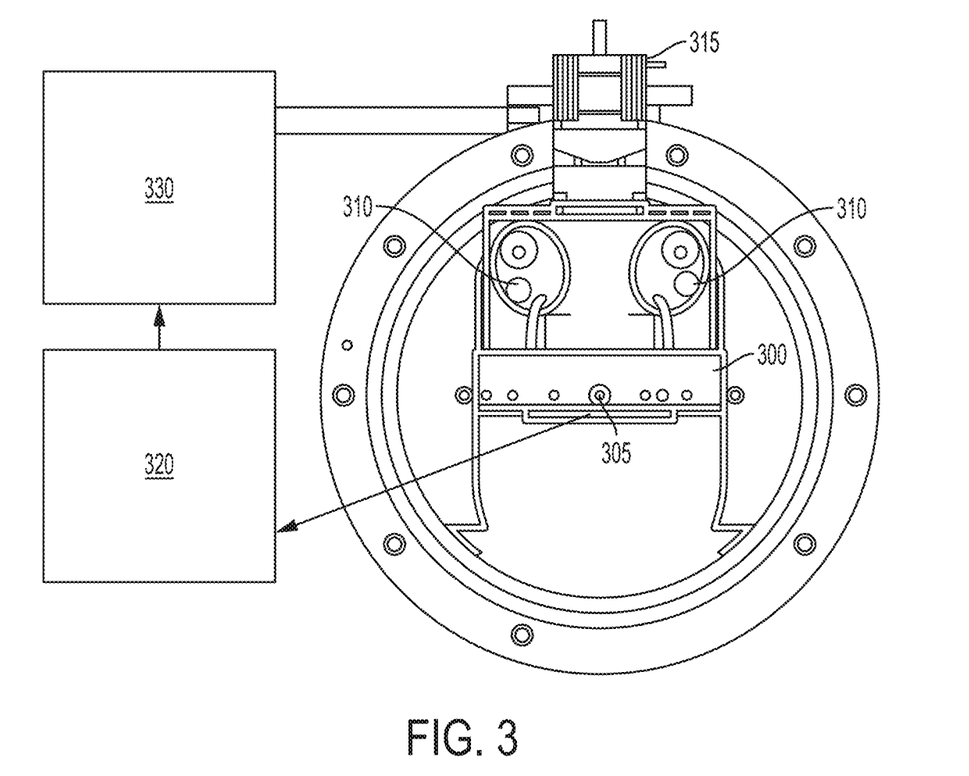
FIG. 3 shows the apex of an example conical shield, including the exit openings of the collimator channels of the collimator wheel and cameras for monitoring the patient.

FIG. 3 shows the apex of the conical shield, including the exit openings of the collimator channels and cameras for monitoring the patient. Collimator wheel 300 is visible edge-on, including selected channel exit aperture 305 and other apertures that are not identified and thus not aligned with the LINAC (underlying and not visible). Motor 315 turns collimator wheel 305 to a selected position in which the desired aperture is aligned with the LINAC. In some embodiments, the system includes one or more cameras to, for example cameras 310, positioned to permit the patient to be monitored while undergoing radiation treatment. Encoder interpretation computer subsystem 320 receives signals from encoder reader heads (see FIG. 2) to compute the precise rotational position of collimator wheel 300, and hence the position of any of the selectable collimator channels. For example, in a feedback loop, motor control computer subsystem 330 serves to activate motor 315 until encoders indicate that the selected collimator is aligned with the LINAC. In one aspect, the system is configured to change the collimator wheel position between multiple positions associated with select collimator channels during therapy so as to differing sizes of treatment beams to the target.

Figure 4:
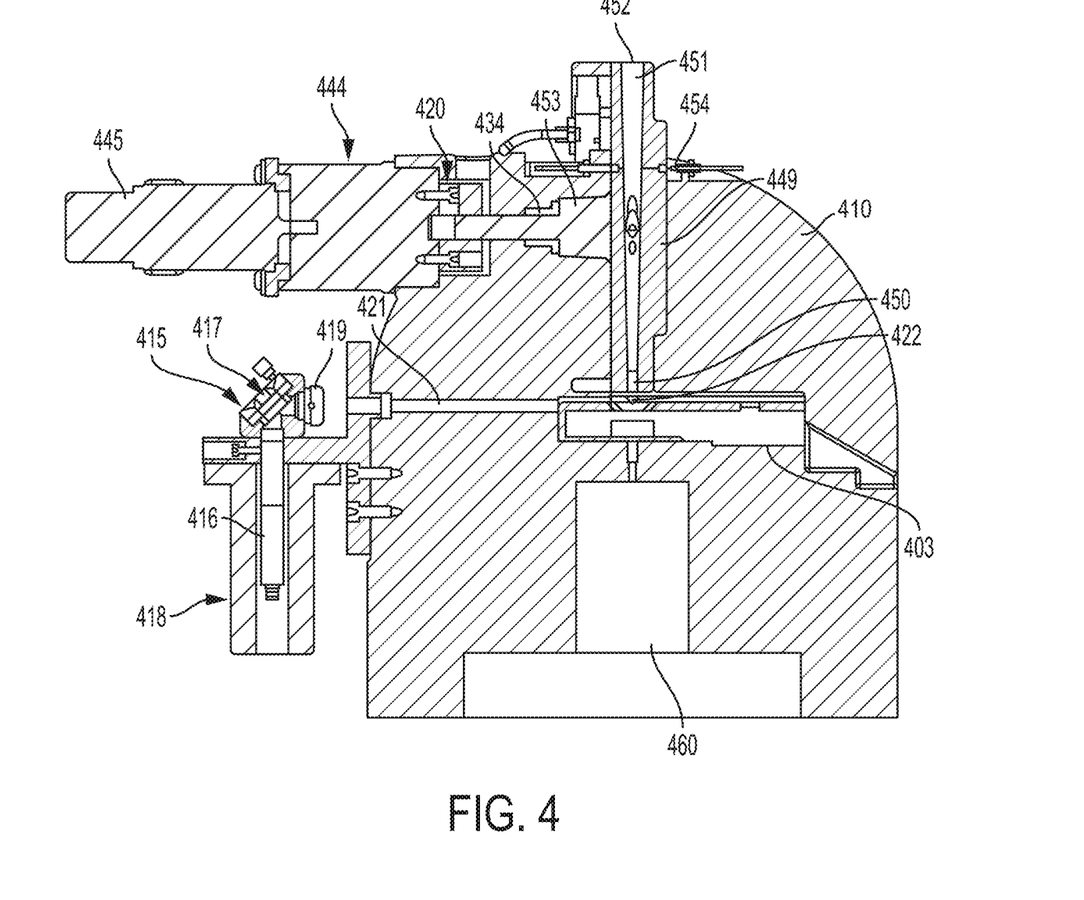
FIG. 4 shows an example collimator wheel and associated motor configured to drive between positions, and a linear accelerator that passes radiation through the collimator wheel and associated features.

FIG. 4 shows a cross-sectional view of the collimator wheel in the context of the motor that drives between positions and a linear accelerator that passes radiation through an aligned collimator channel and associated features.

As shown, collimator wheel 449 has selected and aligned channel 451 with exit aperture 452 and entrance aperture 450. Collimator shield 410 surrounds the collimator wheel 449 along the portion facing the radiation source to allow passage of the particle beam through the inlet and exit orifices of channel 451 while preventing radiation from entering non-aligned channels. In this embodiment, collimator wheel 449 is selectively turned into the desired position via shaft 453 with bushing 434, shaft 453 being connected with gearbox 444 via coupling bracket and base 420. Gearbox 44 is coupled to and driven by motor 445, and provides a reduction in revolutions at a pre-defined ratio, permitting very fine control of the degree to which the collimator wheel is turned and aligned with the radiation source, the LINAC head 460 and distal margin of LINAC body 461. The pre-defined ratio can be 10:1, 20:1, 30:1, 40:1, 50:1, 60:1, 70:1, 80:1, 90:1 or any ratio suitable for a given geometry of the collimator wheel and treatment system and desired resolution of adjustment. In this embodiment, energy exiting LINAC head 460 enters sealed ion chamber 403 which permits monitoring of dose, dose rate and field symmetry by virtue of the fact that radiation that enters the ion chamber will produce a measureable ionization current that is proportional to the x-ray beam intensity.

In this embodiment, mechanical alignment is optimized using optical beam techniques. This has the advantage of maximizing the transfer of radiation from the ion chamber 403 into entrance aperture 450. For this purpose, the system includes laser shield mount holding laser 416, the beam from which is bent at a right angle by mirror 415 and directed into diaphragm iris lens 419 after which the laser light passes through shield bore 421 defined in shield 410 to reach the beam path right angle optical mirror 422. Because the beam path right angle optical mirror 422 is reflective to light but transparent to radiation, a properly aligned collimator can be detected by a laser beam being emitted from exit aperture 452 of collimator 451, while maintaining functionality of the primary radiation delivery alignment, a function useful in initial validation and verification of each machine.

Figure 5:
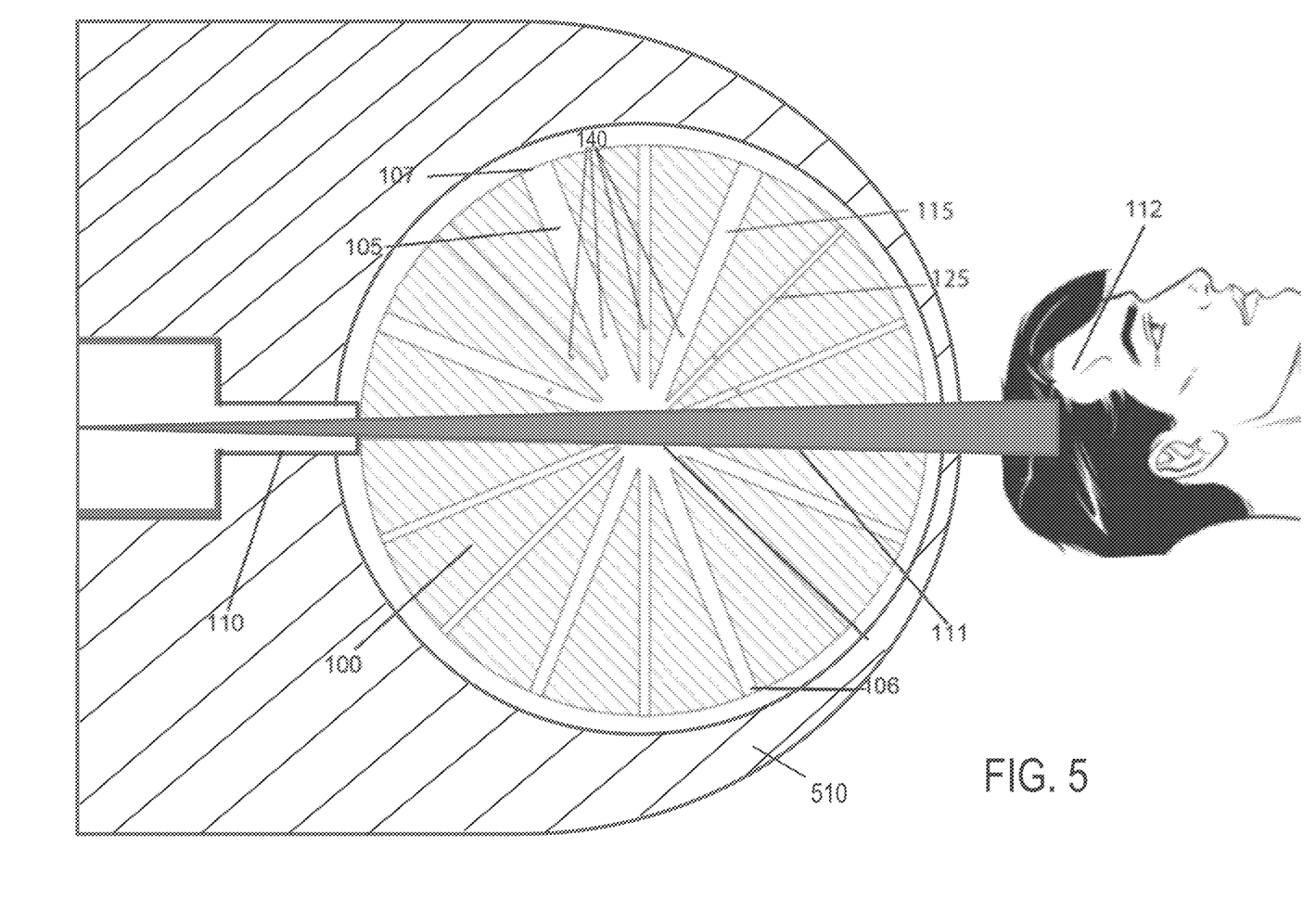
FIG. 5 shows another example conical shield surrounding a periphery of the collimator wheel to cover orifices of non-aligned channels.

FIG. 5 shows another example system with the same or similar collimator wheel and associated components shown in FIG. 1 and a conical collimator shield 510 that substantially surrounds the periphery of the collimator wheel so as to block and absorb radiation emitted from orifices of non-aligned collimator channels while allowing passage of a particle beam 111 from the radiation source 110 through the selected, aligned collimator channel to provide a desired therapy beam to the target 112. In this embodiment, the collimator shield 510 covers any orifices of non-aligned channels, and its resulting greater thickness minimizes radiation leakage from linear accelerator 110. In some embodiments, the shield can cover less than all orifices of non-aligned channels. It is appreciated that in any of the embodiments herein, the shield can include multiple shield components to cover orifices of non-aligned channels and is not required to be a unitary component. Various configurations of the shield can be realized in accordance with the concepts described herein.

While these components are shown in a particular arrangement in this example, it is appreciated that alternative configurations could be realized utilizing various other means of rotating the collimator wheel as would be understood by one of skill in the art. In addition, it is appreciate that certain elements could be omitted, such as the cameras, ion chamber and optical beam alignment features, while still retaining certain advantageous aspects of the invention described above.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A radiation collimator assembly comprising:
   a radiation source comprising a linear accelerator for therapeutic radiation treatment; and
   a collimator wheel rotatable about a rotational axis thereof, the collimator wheel being circular in shape with a diameter, the collimator wheel having a plurality of collimator channels, the plurality of collimator channels including at least:
      a first collimator channel defined within the collimator wheel, and
      a second collimator channel defined within the collimator wheel,
   wherein the first and second collimator channels are arranged substantially perpendicular to the rotational axis of the collimator wheel;
   wherein each collimator channel extends across the entire diameter of the collimator wheel.

2. The radiation collimator assembly of claim 1 wherein each of the first and second collimator channels passes through a center of the collimator wheel through which the rotational axis extends.

3. The radiation collimator assembly of claim 1, wherein the first and second collimator channels are of differing sizes and/or shapes.

4. The radiation collimator assembly of claim 1, wherein the plurality of collimator channels are distributed at regular intervals along the collimator wheel.

5. The radiation collimator assembly of claim 1, wherein the plurality of collimator channels comprises three or more collimator channels.

6. The radiation collimator assembly of claim 1, wherein the first and second collimator channels are selectable by rotationally moving the collimator wheel to align one of the first and second collimator channels with the radiation source.

7. The radiation collimator assembly of claim 1, further comprising:
   a motor operably coupled with the collimator wheel so as to rotate the collimator wheel about the rotational axis; and
   a control unit operably coupled with the motor to control rotation of the collimator wheel to a collimator position corresponding to alignment of a selected collimator channel with the radiation source.

8. The radiation collimator assembly of claim 7 wherein the control unit is communicatively coupled with one or more sensors configured to detect the collimator position.

9. The radiation collimator assembly of claim 8 wherein the one or more sensors comprise one or more encoder readers and the collimator wheel includes a plurality of markers positioned corresponding to alignments of the plurality of collimator channels.

10. A radiation treatment system comprising:
    the radiation collimator assembly of claim 1, wherein the collimator assembly is configured to deliver a radiation beam from the linear accelerator through one or more selected collimator channels of the collimator wheel to a target within a patient;
    a motor operably coupled with the collimator wheel so as to rotate the collimator wheel about the rotational axis; and
    a control unit operably coupled with the motor to control rotation of the collimator wheel to positions corresponding to alignment of one or more selected collimator channels with the radiation source.

11. The radiation treatment system of claim 10, wherein the control unit is configured to rotate the collimator wheel to align one or more selected collimator channels of the plurality with the radiation source, the one or more selected collimator channels corresponding to one or more desired therapy beams.

12. The radiation treatment system of claim 10, further comprising:
    a collimator shield substantially surrounding at least a portion of the collimator wheel facing the radiation source that includes non-aligned collimator channels to inhibit passage of radiation through non-aligned collimator channels while allowing passage of a radiation beam through a selected, aligned collimator channel.

13. The radiation treatment system of claim 10, further comprising one or more imaging devices for monitoring a patient during treatment.

14. The radiation treatment system of claim 10, further comprising:
an optical beam alignment feature configured to monitor or validate alignment of the one or more selected collimator channels with the radiation source.

15. A collimator for collimating a treatment beam generated by a linear accelerator for a therapeutic radiation treatment, the collimator comprising:
a collimator body having a pivot feature about which the collimator body is rotatable about a pivotal axis, wherein the collimator body is a circular shape having a diameter; and
a plurality of collimator channels extending through the collimator body;
wherein each of the plurality of collimator channels is substantially perpendicular to the pivotal axis about which the collimator body is rotated
wherein the collimator body is configured so that each collimator channel extends across the entire diameter of the collimator body.

16. The collimator of claim 15 wherein each of the plurality of collimator channels intersects the pivotal axis.

17. A method of treating a patient with a radiation beam from a linear accelerator of a treatment system, the method comprising:
selecting a first collimator channel from a plurality of collimator channels in a collimator body, the selected first collimator channel corresponding to a desired first therapy beam, wherein the collimator body is rotatable within the treatment system along a rotational axis of the collimator body and the plurality of collimator channels differ in size and/or shape and extend substantially perpendicular to the rotational axis;
rotating the collimator body along the rotational axis thereof until the selected first collimator channel is aligned with the linear accelerator; and
transmitting a first radiation beam from the linear accelerator through the selected first collimator channel so as to direct the first radiation beam to a target within the patient,
wherein the system transmits the radiation beam through only a single selected channel at a time.

18. The method of claim 17, further comprising:
selecting a second collimator channel from the plurality of collimator channels in the collimator body, the selected second collimator channel corresponding to a desired second therapy beam differing from the first radiation beam in size and/or shape;
rotating the collimator body along the rotational axis until the selected second collimator channel is aligned with the linear accelerator; and
transmitting a second radiation beam from the linear accelerator through the selected second collimator channel so as to direct the second radiation beam to the target within the patient.

19. The method of claim 17, wherein rotating the collimator body until the selected first collimator channel is aligned comprises rotating the collimator body until a sensor of a control unit of the system detects a marker disposed on the collimator body indicating a collimator position that corresponds to alignment of the first collimator channel.

20. The method of claim 17, further comprising:
validating alignment of the first collimator channel with the linear accelerator by transmitting a laser light beam through the first collimator channel and detecting the laser light beam emitted from an exit aperture of the first collimator channel.

* * * * *